(12) United States Patent
Van Der Poel

(10) Patent No.: US 11,006,504 B2
(45) Date of Patent: May 11, 2021

(54) EQUIVALENT MELANOPIC LUX (EML) QUOTAS

(71) Applicant: SIGNIFY HOLDING B.V., Eindhoven (NL)

(72) Inventor: Lucas Leo Desire Van Der Poel, Waalre (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 16/767,784

(22) PCT Filed: Nov. 26, 2018

(86) PCT No.: PCT/EP2018/082535
§ 371 (c)(1),
(2) Date: May 28, 2020

(87) PCT Pub. No.: WO2019/105885
PCT Pub. Date: Jun. 6, 2019

(65) Prior Publication Data
US 2020/0367341 A1    Nov. 19, 2020

(30) Foreign Application Priority Data
Nov. 28, 2017    (EP) .................................... 17203989

(51) Int. Cl.
*A61M 21/00* (2006.01)
*H05B 47/115* (2020.01)
(Continued)

(52) U.S. Cl.
CPC ............ *H05B 47/115* (2020.01); *A61M 21/00* (2013.01); *H05B 47/11* (2020.01); *H05B 47/16* (2020.01); *A61M 2021/0044* (2013.01)

(58) Field of Classification Search
CPC ...... H05B 47/105; H05B 47/11; H05B 47/15; H05B 47/155; H05B 47/16; A61M 21/00; A61M 21/0044
(Continued)

(56) References Cited

U.S. PATENT DOCUMENTS

2012/0265350 A1* 10/2012 Ashdown ............. H05B 47/115
                                                                                     700/276
2015/0022093 A1    1/2015   Smith et al.
(Continued)

FOREIGN PATENT DOCUMENTS

EP           3220721 A1    9/2017
WO     2016096367 A1    6/2016
(Continued)

OTHER PUBLICATIONS

Kyle Konis, "A Novel Circadian Daylight Metric for Building Design and Evaluation," Building and Environment 113 (2016) (17 Pages).
(Continued)

*Primary Examiner* — Christopher M Raabe
(74) *Attorney, Agent, or Firm* — Meenakshy Chakravorty

(57) ABSTRACT

A method of determining exposure of an occupant (8) to equivalent melanopic lux, EML, in an environment (2) comprising one or more indoor spaces and zero or more outdoor spaces, wherein the environment comprises one or more illumination devices (4, 5) wherein said one or more illumination devices (4, 5) comprise one or more luminaires (4) illuminating the environment with artificial illumination. The method comprises: —accessing light level information from one or more information sources (6, 12) wherein the light level information comprises information at least on the artificial illumination, and based at least in part on said information on the artificial illumination determining where
(Continued)

in the environment at least a predetermined EML level is present; —using a tracking system (16) to track the occupant within the environment; and —based on this accessing and tracking, monitoring whether the occupant has been exposed to at least a minimum EML quota, the minimum EML quota comprising the occupant being exposed to at least the predetermined EML level for at least a predetermined time period.

14 Claims, 3 Drawing Sheets

(51) Int. Cl.
*H05B 47/11* (2020.01)
*H05B 47/16* (2020.01)

(58) Field of Classification Search
USPC .......................................................... 362/2
See application file for complete search history.

(56) References Cited

U.S. PATENT DOCUMENTS

| | | | |
|---|---|---|---|
| 2015/0161137 A1* | 6/2015 | Lashina | H05B 47/155 707/749 |
| 2015/0204497 A1* | 7/2015 | Grajcar | A01K 29/00 362/2 |
| 2016/0129280 A1 | 5/2016 | Douglas | |
| 2017/0086274 A1 | 3/2017 | Soler et al. | |
| 2017/0135176 A1 | 5/2017 | Soler et al. | |
| 2017/0192406 A1* | 7/2017 | Ashdown | H05B 47/11 |
| 2017/0208673 A1 | 7/2017 | Schlangen et al. | |

FOREIGN PATENT DOCUMENTS

| | | |
|---|---|---|
| WO | 2017037250 A1 | 3/2017 |
| WO | 2017042682 A1 | 3/2017 |
| WO | 2017192566 A1 | 11/2017 |

OTHER PUBLICATIONS

Jessica Zofchak, "Circadian Daylight in Practice. Determining a Simulation Method for the Design Process," Diva Day 2016, University of Toronto 2016 (18 Pages).

Mariana G. Figueiro, et al., "Designing With Circadian Stimulus," ID+A, Oct. 16 (4 Pages).

Robert J. Lucas, et al., "Measuring and Using Light in the Melanopsin Age," Cell Press, Trends in Neurosciences, Jan. 2014 (9 Pages).

Robert J. Lucas, et al., "Irradiance Toolbox User Guide," Oct. 2013 (19 Pages).

L.L.A. Price: "Report on the First International Workshop on Circadian and Neurophysiological Photmetry," 2013 (39 Pages).

* cited by examiner

EQUIVALENT MELANOPIC LUX (EML) QUOTAS

CROSS-REFERENCE TO PRIOR APPLICATIONS

This application is the U.S. National Phase application under 35 U.S.C. § 371 of International Application No. PCT/EP2018/082535, filed on Nov. 26, 2018, which claims the benefit of European Patent Application No. 17203989.3, filed on Nov. 28, 2017. These applications are hereby incorporated by reference herein.

TECHNICAL FIELD

The present disclosure relates to ensuring that an occupant of an environment receives a certain quota of equivalent melanopic lux over a certain time. For instance this could be to ensure compliance with a specification of the WELL (circadian lighting) building standard.

BACKGROUND

WO 2017/042682 A1 discloses a system for computing solar radiation seen by an individual, the system comprising: portable location means for locating and tracking the position of an individual in the course of a day of direct or indirect exposure to the sun; data-collection means containing satellite data d2 regarding solar radiation in the traced position of the individual; computing means operatively connected to said location means and to said data-collection means for receiving data d1 regarding the position of the individual and data d2 regarding solar radiation on the ground in the same position where the individual is in order to compute the dose R1 of solar radiation seen by the individual and to compute a dose R3 of solar radiation that is missing or is in excess with respect to an expected dose R2 corresponding to a desired personal circadian rhythm of the individual.

New lighting recommendations are published in the WELL Building Standard (http://standard.wellcertifled-.com/light/circadian-lighting-design). This defines a recommended melanopic daylight (D65) equivalent, referred to as EML (equivalent melanopic lux), for a variety of scenarios such as work places (e.g. work stations in offices). EML is measured in the vertical plane at a predetermined height above the finished floor corresponding to a typical eye level of the occupant. EML also takes into account luminous intensity and colour temperature. The WELL building standard specifies that EML levels are to be measured during performance verification (the commissioning stage) in order to ensure compliance.

Luminous flux is the measure of the perceived power of light. It is equal to the electromagnetic radiant flux in the visible spectrum weighted per unit frequency according to the luminosity function, which represents the human eye's response to different wavelengths of light. The SI unit is Lumen (lm). Lux (Lx) is the SI unit of luminous flux per unit area (illuminance), a quantity which may be referred to by the symbol E. Sometimes as a shorthand the quantity E itself (as opposed to the SI unit) is referred to as the "lux" (strictly the illuminance). EML is defined as the lux Ev in a vertical plane or vertical cylindrical surface multiplied by a dimensionless ratio MEF (melanopic equivalence factor), referred to in the WELL Building Standard as the melanopic ratio R. The MEF is a function of correlated colour temperature (CCT) of the lux component. It is a metric used to measure the effect of light on a human's circadian rhythm.

The WELL Building Standard®, Version 1.0 of Oct. 20, 2014, downloadable at https://greenplantsforgreenbuilding-s.org/wp-content/uploads/2014/09/THE-WELL-BLDG-STD-102414-FINAL_sml.pdf discloses on page 189-191 the following:

TABLE L1: MELANOPIC RATIO

This unit Equivalent Melanopic Lux (EML) was proposed by Lucas and others (Lucas et al., "Measuring and using light in the melanopsin age." Trends in Neuroscience, Jan 2014). The authors provided a toolbox which for a desired spectrum derives equivalent "α-opic" lux for each of the five photoreceptors in the eye (three cones, rods, and the ipRGCs). The authors selected scaling constants such that each of the values would be identical to each other and the standard definition of lux for a light spectrum of perfectly uniform energy (CIE Standard Illuminant E).

Given a spectrum of light, each equivalent α-opic lux is related to each other by a constant. The table below shows the example ratios between the equivalent melanopic lux and the standard visual lux for several sources.

To calculate the equivalent melanopic lux (EML), multiply the visual lux (L) designed for or measured in a building by this ratio (R): EML=L×R. For example, if incandescent lights provide 200 lux in a space, they will also produce 108 equivalent melanopic lux. If daylight is modeled to provide the same visual brightness (200 lux), it will also provide 220 equivalent melanopic lux.

Similar melanopic ratios can be determined by incorporating the spectrum of the desired source into the calculations in Table L2. Projects are encouraged to use this approach to obtain more accurate results. Both the authors of the journal article and the IWBI have spreadsheets to aid in this calculation.

TABLE L2

MELANOPIC AND VISUAL RESPONSE

| CCT (K) | LIGHT SOURCE | RATIO |
|---|---|---|
| 2950 | Fluorescent | 0.43 |
| 2700 | LED | 0.45 |
| 2800 | Incandescent | 0.54 |
| 4000 | Fluorescent | 0.58 |
| 4000 | LED | 0.76 |
| 5450 | CIE E (Equal Energy) | 1.00 |
| 6500 | Fluorescent | 1.02 |
| 6500 | Daylight | 1.10 |
| 7500 | Fluorescent | 1.11 |

To calculate the melanopic ratio of light, start by obtaining the light output of the lamp at each 5 nm increment, either from manufacturer or by using a spectrometer. Then, multiply the output by the melanopic and visual curves given below to get the melanopic and visual responses. Finally, divide the total melanopic response by the total visual response.

| Wavelength | Light Output | Melanopic Curve | Melanopic Response | Visual Curve | Visual Response |
|---|---|---|---|---|---|
| 380 | ... | 0.00015 | ... | 0.00004 | ... |
| 385 | ... | 0.00031 | ... | 0.00006 | ... |
| 390 | ... | 0.00063 | ... | 0.00012 | ... |
| 395 | ... | 0.00133 | ... | 0.00022 | ... |
| 400 | ... | 0.00285 | ... | 0.0004 | ... |
| 405 | ... | 0.00625 | ... | 0.00064 | ... |

-continued

| Wavelength | Light Output | Melanopic Curve | Melanopic Response | Visual Curve | Visual Response |
|---|---|---|---|---|---|
| 410 | ... | 0.01384 | ... | 0.00121 | ... |
| 415 | ... | 0.02601 | ... | 0.00218 | ... |
| 420 | ... | 0.04887 | ... | 0.004 | ... |
| 425 | ... | 0.07232 | ... | 0.0073 | ... |
| 430 | ... | 0.10624 | ... | 0.0116 | ... |
| 435 | ... | 0.14492 | ... | 0.01684 | ... |
| 440 | ... | 0.19552 | ... | 0.023 | ... |
| 445 | ... | 0.24805 | ... | 0.0298 | ... |
| 450 | ... | 0.31075 | ... | 0.038 | ... |
| 455 | ... | 0.37816 | ... | 0.048 | ... |
| 460 | ... | 0.45413 | ... | 0.06 | ... |
| 465 | ... | 0.53676 | ... | 0.0739 | ... |
| 470 | ... | 0.62557 | ... | 0.09098 | ... |
| 475 | ... | 0.70857 | ... | 0.1126 | ... |
| 480 | ... | 0.79016 | ... | 0.13902 | ... |
| 485 | ... | 0.85767 | ... | 0.1693 | ... |
| 490 | ... | 0.91449 | ... | 0.20802 | ... |
| 495 | ... | 0.95668 | ... | 0.2586 | ... |
| 500 | ... | 0.98081 | ... | 0.323 | ... |
| 505 | ... | 0.98453 | ... | 0.4073 | ... |
| 510 | ... | 0.96695 | ... | 0.503 | ... |
| 515 | ... | 0.9224 | ... | 0.6082 | ... |
| 520 | ... | 0.86033 | ... | 0.71 | ... |
| 525 | ... | 0.78346 | ... | 0.7932 | ... |
| 530 | ... | 0.69706 | ... | 0.862 | ... |
| 535 | ... | 0.60543 | ... | 0.91485 | ... |
| 540 | ... | 0.51274 | ... | 0.954 | ... |
| 545 | ... | 0.42335 | ... | 0.9803 | ... |
| 550 | ... | 0.33998 | ... | 0.99495 | ... |
| 555 | ... | 0.26511 | ... | 1 | ... |
| 560 | ... | 0.20105 | ... | 0.995 | ... |
| 565 | ... | 0.14819 | ... | 0.9786 | ... |
| 570 | ... | 0.10672 | ... | 0.952 | ... |
| 575 | ... | 0.0752 | ... | 0.9154 | ... |
| 580 | ... | 0.05217 | ... | 0.87 | ... |
| 585 | ... | 0.03578 | ... | 0.8163 | ... |
| 590 | ... | 0.02434 | ... | 0.757 | ... |
| 595 | ... | 0.01645 | ... | 0.6949 | ... |
| 600 | ... | 0.01109 | ... | 0.631 | ... |
| 605 | ... | 0.00747 | ... | 0.5668 | ... |
| 610 | ... | 0.00503 | ... | 0.503 | ... |
| 615 | ... | 0.0034 | ... | 0.4412 | ... |
| 620 | ... | 0.00231 | ... | 0.381 | ... |
| 625 | ... | 0.00157 | ... | 0.321 | ... |
| 630 | ... | 0.00107 | ... | 0.265 | ... |
| 635 | ... | 0.00073 | ... | 0.217 | ... |
| 640 | ... | 0.0005 | ... | 0.175 | ... |
| 645 | ... | 0.00035 | ... | 0.1382 | ... |
| 650 | ... | 0.00024 | ... | 0.107 | ... |
| 655 | ... | 0.00017 | ... | 0.0816 | ... |
| 660 | ... | 0.00012 | ... | 0.061 | ... |
| 665 | ... | 0.00008 | ... | 0.04458 | ... |
| 670 | ... | 0.00006 | ... | 0.032 | ... |
| 675 | ... | 0.00004 | ... | 0.0232 | ... |
| 680 | ... | 0.00003 | ... | 0.017 | ... |
| 685 | ... | 0.00002 | ... | 0.01192 | ... |
| 690 | ... | 0.00002 | ... | 0.00821 | ... |
| 695 | ... | 0.00001 | ... | 0.00572 | ... |
| 700 | ... | 0.00001 | ... | 0.0041 | ... |
| 705 | ... | 0.00001 | ... | 0.00293 | ... |
| 710 | ... | 0 | ... | 0.00209 | ... |
| 715 | ... | 0 | ... | 0.00148 | ... |
| 720 | ... | 0 | ... | 0.00105 | ... |
| 725 | ... | 0 | ... | 0.00074 | ... |
| 730 | ... | 0 | ... | 0.00052 | ... |
| 735 | ... | 0 | ... | 0.00036 | ... |
| 740 | ... | 0 | ... | 0.00025 | ... |
| 745 | ... | 0 | ... | 0.00017 | ... |
| 750 | ... | 0 | ... | 0.00012 | ... |
| 755 | ... | 0 | ... | 0.00008 | ... |
| 760 | ... | 0 | ... | 0.00006 | ... |
| 765 | ... | 0 | ... | 0.00004 | ... |
| 770 | ... | 0 | ... | 0.00003 | ... |
| 775 | ... | 0 | ... | 0.00002 | ... |
| 780 | ... | 0 | ... | 0.00001 | ... |
| Totals: | | | ... | | ... |

Note that EML may equivalently also be defined based on other intensity and spectral information indicative of the lux and colour temperature. E.g. using foot-candles as the measure of intensity in the visible spectrum (i.e. illuminance), a factor equivalent to the MEF can be defined which gives the same EML value for illuminance measured in foot-candles as the above equation would for the same illuminance measured in lux.

EML is thus a measure of adjusted lux per unit area in a defined vertical plane or surface. In the norm today it is measured in the vertical plane but it is also possible this will be changed or added to it that it can can also be measured in the cylindrical way. The WELL standard also specifies that such EML levels should be met at specific heights above the finished floor. This is illustrated schematically in Figure 1a and 1b. Figure 1a shows a vertical plane VP through a region of a space such as a room, and a horizontal component Ev of the lux in that space as projected onto an elementary area dA in the plane VP at a height h above the floor. The EML is defined as the lux E falling on dA (the luminous flux per unit area) multiplied by MEF(CCT) where CCT is the colour temperature of the lux component E. FIG. 1b shows the alternative measure of EMF, based on a horizontal component of the lux Ev as projected onto an elementary area dA at a height h on the surface of a vertical cylindrical surface VC. Note the cylindrical surface over which the component is measured doesn't have to be a full cylinder. E.g. the EMF may be averaged over a half cylindrical surface, or measured at an elementary area dA on a cylindrical surface at a particular point.

For work areas, the WELL standard specifies that at least one of the following requirements is met. (a) At 75% or more of workstations, at least 200 EML is present, measured on the vertical plane facing forward, 1.2 m above finished floor. This light level may incorporate daylight, and is present for at least the hours between 9:00 am and 1:00 pm for every day of the year. (b) For all workstations, electric lights (which may include task lighting) provide maintained illuminance on the vertical plane facing forward of 150 EML or greater.

Breakrooms: for workplaces where employees spend most of their time in spaces with light levels limited by work type (such as restaurant servers or hospital ward workers), the WELL standard specifies that such workplaces have break rooms which meet the following requirement. Lights provide a maintained average of at least 250 EML as measured on the vertical plane facing forward at surfaces 1.2 m above finished floor. The lights may be dimmed in the presence of daylight, but are able to independently achieve these levels. In living environments (e.g. bedrooms, bathrooms, and rooms with windows), the WELL standard specifies the following. (a) 200 or more EML as measured facing the wall in the centre of the room 1.2 m above the finished floor. The lights may be dimmed in the presence of daylight, but are able to independently achieve these levels.

(b) Lights provide not more than 50 EML (to the extent allowable by code) as measured 0.76 m above the finished floor.

In learning areas, the WELL standard specifies that at least one of the following requirements is met. (a) Early education, elementary, middle and high schools, and adult education for students primarily under 25 years of age: the light (which may incorporate daylight) must provide at least 125 EML at 75% or more of desks, on the vertical plane facing forward 1.2 m above finished floor. This light level is present for at least 4 hours per day for every day of the year. (b) Ambient lights provide maintained illuminance on the vertical plane of EML greater than or equal to the lux recommendations in the Vertical (Ev) Targets in Table 3 of IES-ANSI RP-3-13, following the age group category most appropriate for the population serviced by the school. For example, art studios in elementary school, middle school, or high school are provided with 150 EML from the electric lights.

Separately from the WELL standard, one known technique for monitoring a person's exposure to light is to wear a wearable light sensor device on a pendant around the neck.

SUMMARY

In flexible offices today, people often work at many different locations during the day and in different settings. For instance the workplace can be a standard or open office, a focus room or a small or big meeting room. Often the person's activities will be spread over several spaces over the working day. This presents a challenge for ensuring the person (the occupant) receives at least a minimum quota of EML over a certain time, e.g. per day or within one or more specified time windows per day. For instance it may be desired to ensure compliance with one, more or all of the quotas specified in the WELL standard. Or in general, other alternative or additional quotas may be defined.

According to one aspect of the present disclosure, there is provided a method of determining exposure of an occupant to equivalent melanopic lux, EML, in an environment comprising one or more indoor spaces and zero or more outdoor spaces. The method comprises: accessing light level information from one or more information sources, and based thereon determining where in said environment at least a predetermined EML level is present; using a tracking system to track the occupant within said environment; and based on said accessing and said tracking, monitoring whether the occupant has been exposed to at least a minimum EML quota, the minimum EML quota comprising the occupant being exposed to at least said predetermined EML level for at least a predetermined time constraint.

Thus the present disclosure advantageously provides an intelligent tracking system to measure the received EML light for a person, in order to check whether a minimum quota is received (e.g. to check whether the quota as specified by the WELL building standard is met). As the EML is measured for different locations (e.g. on a per room basis) and the location of the occupant is tracked, it is possible to determine whether the person has received his or her EML quota despite the fact that he or she may enjoy a flexible working regime involving moving between a number of different rooms or other such spaces throughout the day.

The disclosed technique also improves over the use of a wearable sensor, which has the disadvantage that the user may forget to wear the device, and it can also easily be covered by other pieces of clothing or even by the user's own arm.

In embodiments, the disclosure provides an EML calibration of different spaces in a building, and uses these calibrated EML levels in combination with a people tracking system to monitor if and when an individual has reached his/her daily EML exposure. This may be advantageous in maintaining WELL certification for buildings and/or building projects.

In embodiments, the system may also track when a person went outdoors, e.g. for a walk, and estimate the received outdoor EML based on one or more sources such as outdoor sensors and/or local weather information.

The environment may for example comprise multiple indoor spaces, e.g. each being a different room (e.g. offices, breakrooms, corridors, etc.). Optionally the environment covered by the tracking may also include one or more outdoor spaces, e.g. a workspace, garden, outdoor smokers' area, or the exterior parts of a campus, etc. The one or more information sources can take a number of different forms, such as a commissioning database, a network of light sensors, and/or a network such as the Internet form which current outdoor light levels can be obtained (e.g. from an online weather report).

The determination of where the predetermined EML level is met may be performed on a space-by-space basis, e.g. a per room basis, or split into smaller areas. For example an average EML may be determined for each room or space, or the EML at a representative location in each room may be determined (such as a work station or the centre of the room or space). As another example a room may be split into different areas such that the tracking system will know in which area of the room the occupant is spending time. The average per room or zone may be an omnidirectional average; or the average or representative value may be the value in a specified direction, such as the direction defined by the WELL standard. Either way, the measurement of whether the occupant receives the EML may then be based on assuming that when the user is in a given space, he/she receives approximately the average or representative EML for that space.

In other implementations the tracking may track when the user is stationed at an identified one of a set of predetermined stations such as one of multiple work stations. The information source may only provide data for the set of predetermined stations, e.g. pre-stored EML values or sensor readings specifically for each possible station. The measurement of the occupant's total EML is then based on the time spent at each of the stations, e.g. each work station, combined with the known EML at each such station (assuming that time between stations is approximately negligible).

In further embodiments "traffic zones" can be taken into account so walking across a corridor between stations or other rooms contributes to the monitored total as well.

In yet further alternative implementations, the information source may map out the EML levels on a more granular point-by-point basis (i.e. information for multiple sets of coordinates throughout each space, such as multiple sets of coordinates in each room). For example with indoor positioning and/or other new technologies, the system will be able to follow quite accurately where time is spent. In such cases, the tracking system may track the user's point location and determine what EML the occupant receives at each respective point. In some embodiments the information from the information source is not directional, so the measurement stage assumes the EML is approximately the same in all directions at a given point. Alternatively the information may be directional and the tracking system may also track which direction the occupant is facing in, e.g. using facial recognition or by tracking his/her direction of travel, or even simply by assuming that when sitting behind a desk or screen the main viewing direction is known. In such cases the directional EML can be used to determine the occupant's total quota.

In embodiments, the illumination devices may comprise one or more luminaires illuminating one or more of the spaces with artificial illumination, and the light level information may comprise information on at least the artificial illumination, said determination being based at least in part on said information on the artificial illumination.

In embodiments, the one or more information sources may comprise a database, and said light level information may comprise data from the database mapping out light level values indicative of EML in said environment, said determination being based at least in part on the values in the database.

The values in the database may be pre-calculated or pre-measured. This may be based on a pre-performed calibration of the luminaires, for instance from an installation or commissioning phase. The values as stored in the database could be the explicit EML values themselves, in which case the determination step simply comprises directly reading the EML values from the database. Alternatively the values in the database could be another measure of spectral power that is indirectly indicative of EML, such as intensity, lux or luminous flux along with colour temperature or other such spectral information, or even full power spectral density values. This can then be converted to EML as part of the determination step. The database could be local, in the same environment as the lighting, or could be remote, e.g. accessed over a network such as the Internet.

As another example, in case of a luminaire with a settable colour temperature or spectrum, such as a tuneable white luminaire, a controller controlling the tuneable white luminaire may be arranged to communicate the actual current spectrum or colour temperature setting to the database in real-time. In case of dimming and a tuneable spectrum, both the dim level and colour settings may be communicated to the database in real-time. Different pre-stored or pre-measured values may be stored in the database for each possible setting, or only some different pre-stored or pre-measured values may be stored in the database and the controller may be configured to extrapolate between them based on the communicated setting(s). As another example, the values in the database may be flexible so that they are updated in real-time in accordance with the communicated setting(s).

Alternatively or additionally, the environment may comprise one or more outdoor spaces, and/or the environment may comprise one or more indoor spaces and the illumination devices may comprise one or more window treatments. In such cases the light level information may comprise dynamic information on natural daylight, said determination being based at least in part on said information on the natural daylight.

In embodiments the one or more information sources may comprise a communication network providing a report on current daylight conditions, said determination being based at least in part on said report.

For instance, the information source could be an online weather report. In this case the accessing step may comprise accessing from the weather report, over the network (e.g. the Internet), information on general outdoor ambient light conditions in the vicinity. The determination step will then comprise approximating the EML component based on knowledge of the ambient light conditions. For instance the report could give explicit EML values, or could give other intensity and spectral data from which a controller can derive the EML. Alternatively, the report could instead give indications such as "sunny" or "overcast" and the controller may then determine the EML based on knowledge of the intensity and spectrum of daylight on a sunny or overcast day (perhaps also as a function of the geographic location of the environment in question, and/or linked to a calendar since light intensities will differ over the year). In embodiments the computed EML may also be a function of the physical layout and/or orientation of the environment.

In yet further alternative or additional embodiments, the one or more information sources may comprise a network of light sensors each arranged to measure light level information at a different respective horizontal location within the environment at said predetermined height, and said determination may be based on said measured light level information.

In embodiments the sensors may be spectrally sensitive light sensors each arranged to measure, at a different respective horizontal location within the environment, the measured light level information comprising a light power spectrum or light power spectral distribution in a vertical plane or surface at said predetermined height, said determination being based on said measured light level information.

In embodiments, the tracking system may be able to predict, based on observation of past routine of the occupant, where the occupant is likely to move to later within the time period in question (e.g. later in the day). This may be taken into account when adapting the lighting to balance EML requirements vs. other factors such as power saving or ambience. For instance it may be desired to predict if the occupant will get enough EML before the expiry of the period 9:00 am-1:00 PM as specified in the WELL standard.

In embodiments, the method may comprise using a timer in conjunction with said accessing and tracking to predict whether the occupant will be exposed to said predetermined EML quota, and if not automatically controlling the illumination to increase the EML level in at least one region of the environment that the occupant is occupying or is predicted to occupy later.

Alternatively or additionally, the method may comprise automatically reducing an intensity and/or colour temperature of at least some of the illumination, or switching off at least some of the illumination, so as not to meet said predetermined EML level in at least one region of the environment where the occupant is determined not to be currently present based on said tracking, or after the occupant has already been exposed to the minimum EML quota or it is predicted that the occupant will be exposed to more than said minimum EML quota.

Although there is not believed to be any maximum EML the occupant should be exposed to, it may still be desirable to turn off or dim down the illumination in one or more spaces, or to change its colour temperature, for reasons other than EML such as saving energy. For instance in spaces the occupant is not currently occupying or is predicted not to occupy for the rest of the day, the light could be turned off. Or once it is determined that the occupant is likely to overshoot his/her EML quota for the day, then in order to save power light levels in a room he or she is occupying or is predicted to occupy could be dimmed down and/or set to a lower (less blue) colour temperature. For example this could be done once it is late afternoon or evening time and the occupant has already had his/her EML quota for the day.

E.g. after the EML quota for the 9 am-1 pm period has been met, and especially the later it gets in the day, the more blueish light should be avoided, so after 1 pm the blue light component may be automatically lowered over time.

In further embodiments, the method may comprise, based on said accessing and tracking, automatically informing the occupant or another user via a user interface one or more of: (i) whether the occupant has been already exposed to the minimum EML quota, (ii) whether it is predicted the occupant will be exposed to the minimum EML quota, and/or (iii) a running measure of current EML exposure of the occupant.

In embodiments, the predetermined EML level may be the EML at least one predetermined height above the floor. For example the predetermined height may be 1.2 m, 1.5 m, or a height between 1.2 and 1.7 m.

In embodiments said predetermined EML level is equal to or greater than 125 EML. In embodiments said predetermined EML level is equal to or greater than 150 EML. In embodiments said predetermined EML level is equal to or greater than 200 EML. In embodiments said predetermined EML level is equal to or greater than 250 EML. In embodiments said predetermined EML level is equal to one of: 125 EML, 150 EML, 200 EML or 250 EML.

In embodiments said predetermined time constraint may comprise at least a requirement that the occupant is exposed to at least said predetermined EML level for a minimum period of time within a predetermined time window of: a day, a working day, the hours of daylight in a day, or a morning between 9 am and 1 pm; wherein the time constraint resets each day.

In embodiments, said predetermined time constraint may be that the occupant is exposed to at least said predetermined EML level for at least three hours between 9 am and 1 pm.

As another example, in embodiments said predetermined time constraint may be that the occupant is exposed to at least said predetermined EML level for at least 4 daytime hours during the day, with at least two of these hours per day between 8 am and 11 am.

According to another aspect of the present disclosure, there is provided control apparatus configured to perform operations in accordance with any of the methods disclosed above or elsewhere herein. The control apparatus may be implemented in the form of dedicated hardware logic, or memory and processing apparatus programmed to perform the disclosed method, or any combination of the two approaches.

According to another aspect of the present disclosure, there is provided a computer program product embodied on computer-readable storage comprising one or more memory units, configured so as when run on processing apparatus comprising one or more processing units to perform operations in accordance with any of the methods disclosed above or elsewhere herein.

According to another aspect disclosed herein, there is provided a system for determining exposure of an occupant to equivalent melanopic lux, EML, in an environment comprising one or more indoor spaces and zero or more outdoor spaces, the system comprising: one or more sources of light level information indicative of where in said environment at least a predetermined EML level is present; a tracking system to track the occupant within said environment; and a controller arranged to access the one or more sources and based thereon determine where in said environment at least the predetermined EML level is present; wherein the controller is further configured to use the tracking system to track the occupant within said environment, and based on said accessing and said tracking, to measure whether the occupant has been exposed to at least a minimum EML quota, the minimum EML quota comprising the occupant being exposed to at least said predetermined EML level for at least a predetermined time constraint.

According to another aspect of the present disclosure, there is provided an EML sensor for use with a lighting system, the EML sensor comprising: a light sensor for installation in a space for occupying by one or more occupants and illuminated by one or more luminaires of the lighting system during an operational stage after commissioning of the lighting system, wherein the light sensor is configured to measure light level information indicative of spectral power of light at a predetermined height above a floor of the space; and sensing logic arranged so as, during said operational stage, to automatically compute an EML level of the light at said predetermined height. The logic may be implemented in software or hardware or any combination thereof.

BRIEF DESCRIPTION OF THE DRAWINGS

To assist understanding of the present disclosure and to show how embodiments may be put into effect, reference is made, by way of example only, to the accompanying drawings in which.

DETAILED DESCRIPTION OF EMBODIMENTS

Figure 1A:
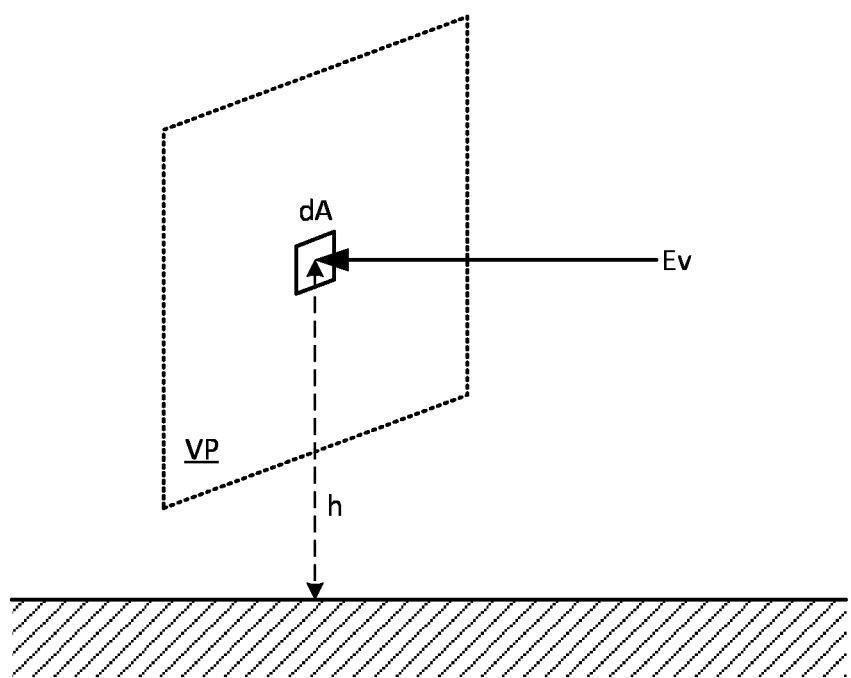
FIG. 1a schematically illustrates EML on a vertical plane.

The following describes the use of an information source such as a database of EML levels per area in an environment such as building. The EML levels can either be measured based on the cylindrical illumination or planar illumination with an illuminance Ev at a predetermined height such as 1.2 m (corresponding to typical seated eye height) and/or 1.5 m (corresponding to typical sanding eye height) combined with a colour temperature to indicate the EML for a specific area. When bases on cylindrical illumination, the center of the cylinder may represent the position of a user in the specific area and the cylindrical surface represents the 360° viewing directions that the user in that position may look into. In a typical office work place it may be sufficient to only consider a 180° cylindrical surface to cover the possible viewing directions of a person present at the office work place and determine an average EML for that location. Alternatively or in addition, the EML levels can be calculated with special software like DIALux (https://www.dial.de/en/dialux/) to find the vertical cylindrical or planar illumination levels at specific heights in specific areas. By linking this database with a tracking system it is possible to follow a person and calculate the time spent in a particular space and the EML exposure received in that space. This will result in a cumulation of received EML levels giving a total dose over time for a period such as a day. The tracking system may for example be based on RFID access using personal RFID tags and RFID scanners in every space. Alternatively, a tracking system based on indoor positioning may be used. Further, other sources of light level information can be used, such as sensors, or a dynamic report such as an online weather or light level report accessed via a network such as the Internet.

The intelligent tracking system can thus be used to measure whether a person in a building (and/or outside) has received the minimum quota of EML light for a period such as a day, e.g. one of the quotas specified in the WELL building standard. The idea is to install lighting installations in a building or other environment and calculate or measure in that building or environment the EML levels (e.g. Ev at 1.2 m and/or 1.5 m height combined with a certain colour temperature) for all areas. This can also be done with existing lighting installations. The combination of Evc (vertical cylindrical illumination level or vertical planar illumination level and colour temperature (CTT) will indicate the received EML for a specific area. By setting all the EML values in a database for all these areas and by measuring the time persons spend in specific areas it will be possible to calculate the amount of EML exposure a person has received in specific time intervals. This makes it possible not only to make WELL compliant building lighting installations but also to prove that a person has received the minimal ELM quota(s). If the exposure is too low, extra measures can be offered, e.g. adapting the lighting to increase EML exposure for rest of the day, or triggering an additional light source (e.g. a dedicated EML lighting device, or increasing the brightness and/or colour temperature of a screen in front of which the occupant is sitting for a short time). Further, it will be possible to add information for outdoor circumstances. For example when a person goes out for a lunch walk the system may register that the person leaves the building, and local light-weather information can be added from the Internet or a light sensor (e.g. a local sensor such as a sensor on the roof of the building, or a central sensor on the building campus). For example it may be determined that a person walks for 30 min outdoor in the sun with an EML of 1000, and this value may be added to the total EML received.

As mentioned, for work places like work stations in offices new recommendations are published in the WELL standard. According to the WELL standard all work stations should have a melanopic daylight (D65) equivalent (EML=equivalent melanoptic lux) illuminance of at least a certain value, e.g. 250 EML, for specific hours during the workday. As a proxy for the human observer sitting at any given position in the space, a calculation grid 1.2m above the finished floor shall be used to determine the average cylindrical EML illuminance in the space, or the average vertical planar EML illuminance in the space. According to one example, the minimal EML illuminance is present for at least 4 daytime hours for every day of the year, preferably in the morning, with at least 2 of these hours between 8 am and 11 am.

The EML is measured in the vertical plane or in cylindrical terms. In the WELL standard it is described what the EML levels should be for different use cases. Since the measure should preferably be omnidirectional the light should preferably come from all around. There is also a ratio connected to the needed level, the MEF factor, which is a function of colour temperature (and which can be calculated either directly based on an explicit CCT value or indirectly based on other intensity and spectral information indicative of the CCT). The warmer the light the higher the illumination level has to be to get the same EML level.

In practice however, in flex offices today people work at many different locations during the day and in different settings. The work place can be a standard or open office, a focus room or a small or big meeting room. Often their activities will be spread over several spaces over the working day.

Embodiments herein provide a solution whereby all EML levels are calculated or measured in one or more valid planes or surfaces (e.g. 1.2 and/or 1.5 meters above the floor) in some or all of the different spaces within a specific building. The system can also be extended to various buildings. The EML values for all specific areas are then set and collected in a database (or equivalently lighting information from which EML can be derived, e.g. lux and colour temperature data). So the database contains a full overview of all the different EML levels in a building. Now with help of a tracking systems such as indoor positioning systems or RFID scanners (preferably at least one in every space), it will be possible to track in which spaces a person is spending his/her time. By multiplying the EML value of a specific space with the time spent in this space it will be possible to calculate how much EML a person is receiving over time. In this way every individual can keep track of his/her received EML exposure. This will give the option to calculate whether the minimum EML levels are reached or not. If the levels are not reached there are options to increase the EML levels to make sure persons will receive the minimal amount of EML. This can be done for example with personal EML light in vertical planes or by increasing the overall (EML) lighting levels in the space one is working in. The personal EML light may for example be provided by a dedicated EML lighting device(s) associated with the occupant's work station, or by means of a bright screen which the occupant sits in front of Here one can increase the lighting level and/or the colour temperature to reach the levels needed within the preferred time interval.

In embodiments, the solution is made possible by making a database of all EML levels in a building. This can be done by measuring or by calculations with special software (like DIALux) to find the cylindrical or planar illumination levels at specific heights for the different areas. Next all data for all spaces is collected in a database. This database is linked with a tracking system, such as an RFID system comprising RF tags which are person connected (for example in a person's company ID card or other solution to fix a RFID tag to a person) and RFID scanners in every space. Thus it is possible to follow a person and to calculate how much time is spent in the preferred time intervals in specific spaces. Since the EML values for these spaces are known it is possible to calculate how much EML a person received during the time passed by. There may also be options to track the presence of persons with help of other means such as indoor positioning. In that case for example VLC (visible light communication) enabled luminaires can take over or supplement the function of RFID scanners. Further, an alternative or additional approach to using the database is to use a network of dynamic sensors disposed throughout the environment to dynamically sense actual current EML levels.

Figure 2:
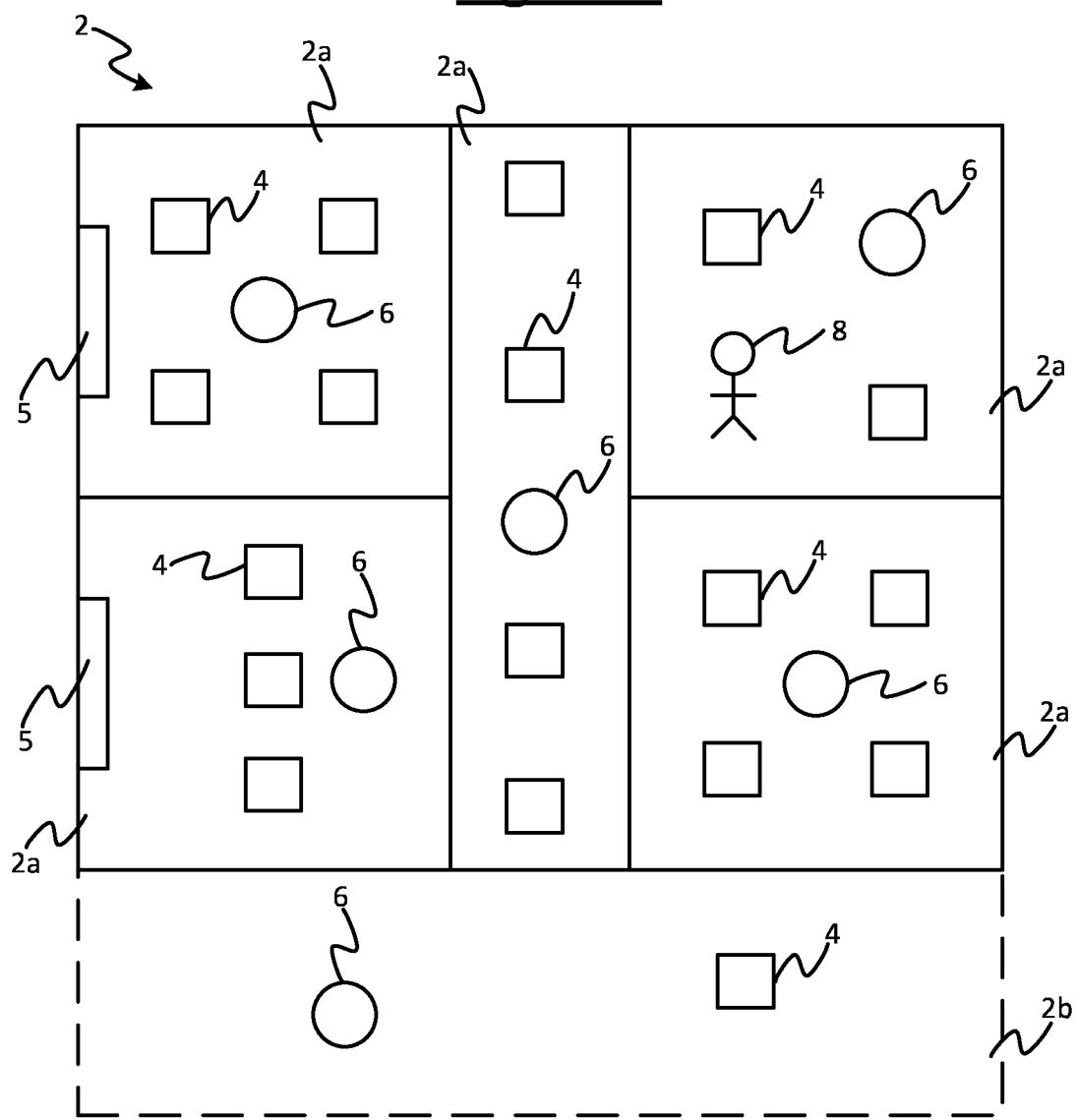
FIG. 2 is a schematic plan view of an illuminated environment.

FIG. 2 illustrates an example lighting system in accordance with embodiments disclosed herein. The system is installed in an environment 2 occupied by at least one occupant 8 (a human). The environment 2 comprises one or more indoor spaces 2a and optionally one or more outdoor spaces 2b. Each indoor space may comprise a respective room of a building, e.g. an office room, a meeting room, a breakroom, a canteen, a foyer or reception, or a corridor and the various rooms may include different such types of room. Or in the home the rooms may comprise a living room, kitchen, bathroom, one or more bedrooms, etc. Examples of outdoor spaces 2b include a garden, a quadrangle, the exterior parts of a campus, a park, or any outdoor area where the occupant might move to before, after or in between occupying one or more of the indoor spaces 2a. The occupant 8 is free to move between some or all of the different spaces 2a, 2b, e.g. as part of his/her working day or day generally.

The lighting system comprises one or more lighting devices, comprising one or more luminaires 4, and/or one or more window treatments 5 (curtains, blinds or shutters for controlling the amount of light entering an indoor space 2a through a window). Preferably there is at least one lighting device (e.g. a luminaire or window treatment) 4, 5 in each of the indoor spaces 2a. Optionally one or more luminaires 4 may be provided in the outdoor space(s) 2b, e.g. for the sake of workers doing outdoor night shifts or in latitudes with little or no daytime daylight in winter. Each luminaire may take a variety of forms (and different luminaires 4 could take different forms), for instance a ceiling mounted luminaire, a luminaire mounted on a wall such as a wall washer, a free standing luminaire (e.g. a floor lamp, table lamp or desk lamp), or less traditional forms such as a luminaire embedded in a surface or an item of furniture. The luminaires 4 may include task lights and/or ambient lighting. In the case of window treatments 5, these could be manual or automated. The lighting devices 4, 5 provide illumination into respective spaces 2a, 2b of the environment 2.

Note that windows or window treatments are not necessarily taken into account. In embodiments, the system may not consider any daylight and any daylight entering through windows could be treated as 'bonus' illumination.

Figure 1B:
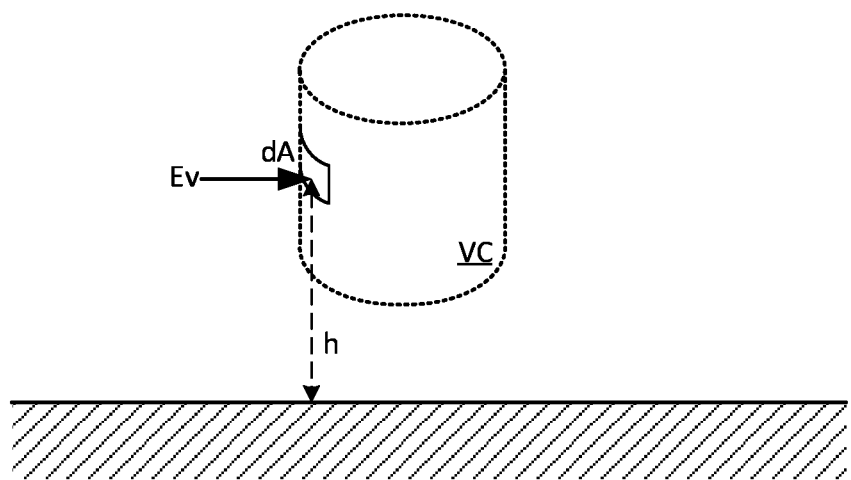
FIG. 1b schematically illustrates EML on a cylindrical surface.

The lighting devices 4, 5 between them provide, in each space 2a, 2b, both a downward component of illumination (a flux through a horizontal plane) and a sideways component of illumination (a flux through a vertical plane or surface as shown in FIGS. 1a and 1b). This may be achieved by means of separate downward facing and sideways facing luminaires 4 or generally lighting devices 4, 5 illuminating a given space 2a, 2b. And/or, the downward and sideways components may be provided by a given luminaire 4 arranged to emit both a horizontal and vertical component, for example by being slanted at an angle.

Figure 3:
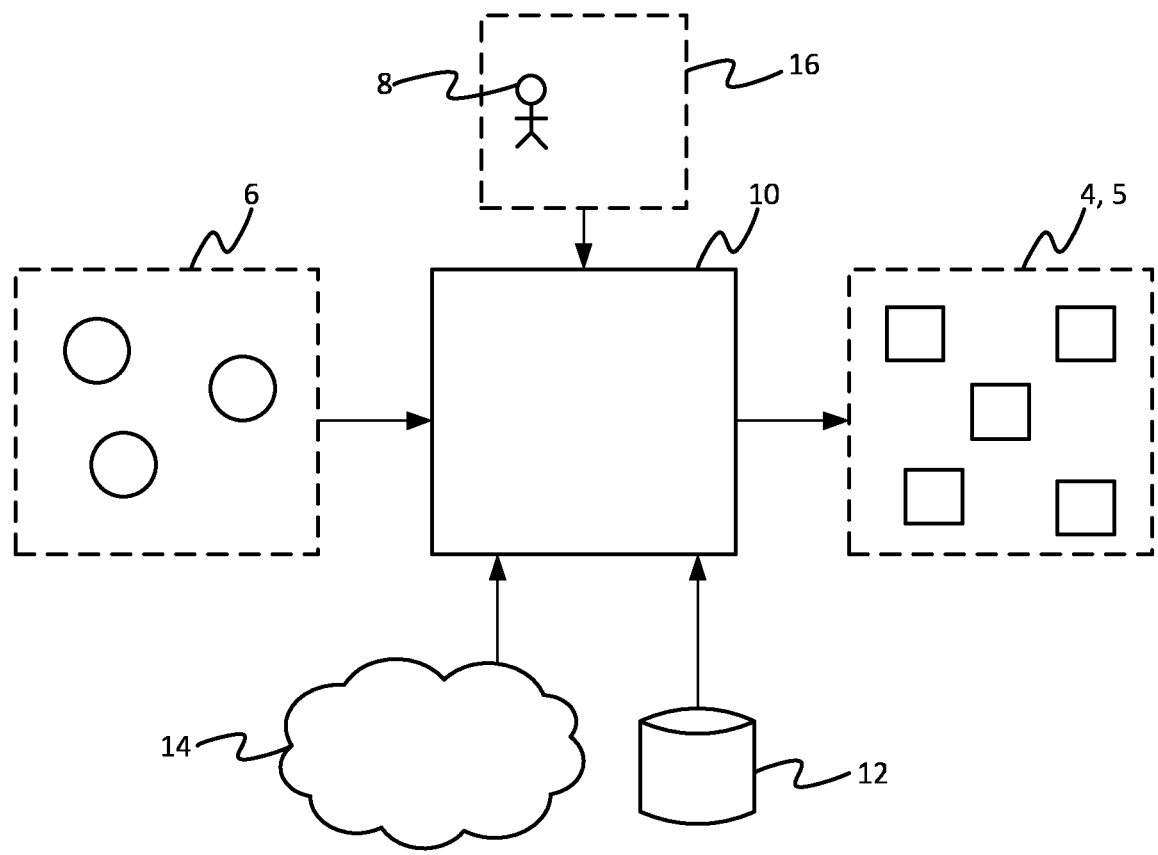
FIG. 3 is a schematic block diagram of a control system.

Turning to FIG. 3, the system further comprises a controller 10 and a tracking system 16. The controller 10 is operatively coupled to the luminaires 4 in order to control the intensity and/or colour temperature of the illumination emitted by the luminaires 4 into their respective parts 2a, 2b of the environment 2. In embodiments the controller 10 may also be coupled to one or more of the window treatments 5 and thereby able to control the amount of light admitted through a respective window by the window treatment 5, e.g. in the case of an electrically controllable blind, curtain or shutter. The coupling between the controller 10 and such lighting devices 4, 5 may be via any wired and/or wireless means, e.g. via a wired network such as an Ethernet or DALI network, or a wireless network, e.g. a wireless local area network (WLAN) such as a Wi-Fi or ZigBee network, or any combination. Various means of communicating between subsystems of a system will be familiar to a person skilled in the art and will not be discussed at length herein. The controller 10 may be implemented in the form of software stored on one or more memory devices and arranged to run on one or more processing units. Alternatively the controller 10 may be implemented in hardware, or any combination of hardware and software. The controller 10 may be implemented on any suitable physical unit or units. E.g. it may be implemented on a server, a lighting bridge, or a dedicated control unit; or it may take the form of a distributed function implemented throughout multiple components of the system such as in the luminaires 4 themselves, or a combination of server and bridge, or server and luminaires, etc.

The controller 10 is also coupled to the tracking system 16. Again this coupling may be via any wired and/or wireless means, such as those discussed above in relation to the luminaires 4, though the same communication means need not necessarily be used. The tracking system is arranged to track the location of the occupant 8 throughout the environment 2 and to provide information on the tracked location to the controller 10. The tracking system 16 may take any of a variety of forms. In embodiments the tracking system 16 comprises an RFID tracking system, comprising an RFID tag disposed about the person or the occupant 8, and a plurality of RFID readers disposed throughout the environment 2, preferably at least one in each space 2a, 2b (e.g. each room). For instance there could be an RF reader at each of a plurality of work stations in different parts of the environment 2, e.g. different rooms 2a. When the user enters a given space 2a, 2b, or sits at a given work station, etc., then he/she explicitly or implicitly scans his/her tag against the reader and hence registers his/her location at that place with the controller 10. E.g. each occupant 8 has an RF tag in an ID card and a gate with RF reader is arranged every internal and/or external door so that when people pass through they are recognized, and the system knows on constant basis in which space a person is. As another example, the occupant 8 may explicitly scan entrances or exits of the building, so that the controller 10 knows when the user enters or leaves the building. In an equivalent arrangement the RF tags and reader could be reversed (i.e. the occupant has an RF reader disposed about his person and RF tags are located at different places throughout the environment).

Further, other alternative or additional location tracking systems are known in the art and can be used for the present purposes. These may for example be based on the occupant having another type of device such as a mobile smartphone, smartwatch or wearable user terminal disposed about his/her person. For instance the tracking system 16 may comprise an indoor location system comprising a network of anchor nodes located throughout the environment 2, in which case the location of the occupant 8 is detected based on wireless beacon signals exchanged in one direction or the other between the anchor nodes and a wireless device (e.g. a mobile phone) disposed about the occupant's person, using a calculation such as triangulation, trilateration, multilateration or fingerprinting. In one particular example the beacon signals are coded light signals embedded in the light emitted by the luminaires 4 themselves, detected by a light sensor such as a camera in the occupant's device (e.g. their smartphone, smartwatch or wearable camera). In another alternative or additional example, the tracking system 16 may comprise a network of cameras installed throughout the environment 2, configured to detect the occupant based on image recognition, e.g. facial recognition. Various tracking technologies are known in the art and will not be repeated here at length.

Further, in embodiments, the system comprises a database 12, which is also operatively coupled to the controller 10. In embodiments the database may be implemented on the same physical unit as the controller 10, e.g. same server or lighting bridge. Alternatively the database is implemented elsewhere and is coupled to the controller 10 via any suitable wired or wireless communication means, e.g. a wired or wireless LAN (e.g. Ethernet, Wi-Fi, etc.) or even a wide area network such as the Internet.

The database 12 maps out light level information throughout the environment and resulting from the luminaires 4 (i.e. due to artificial light), wherein this information reflects both the intensity of the light and the spectrum of the light. The information in the database 12 may be determined at a commissioning phase prior to a subsequent operational phase, the operational phase being when the system is in actual normal use, after installation and commissioning is complete, possibly with the occupant 8 being present and his/her EML exposure being monitored by the controller 10. Alternatively or additionally, the information in the database may be populated dynamically during the operational phase, such as based on light sensor readings or current user settings. In the case of commissioning, note that the measured or calculated EML right after finishing a new installation will be higher than some time thereafter, since LEDs or indeed any lighting sources in general will give less light output over time. In embodiments this may be taken into account in the commissioning phase by installing luminaires with a slightly higher light level than required to be able to meet the requirements some time later, e.g. after two years.

In embodiments the database 12 may store different values of the information for different times of day (for example for luminaires controlled to provide extra EML in the morning hours). And/or, the database 12 may store different values of the information for possible dim-level and/or colour settings, which may be set automatically or manually by a user. The controller 10 may then look-up the relevant information for the current time of day and/or light settings. As a variant of this the database may store a smaller number of light level settings and the controller 10 may extrapolate between these based on the current setting(s). As another variant, the information in the database may be updated dynamically based on the current setting(s).

This information in the database 12 may take a variety of forms. In embodiments the information may be actual EML values, i.e. EML values are stored directly in the database 12. The EML values indicate the EML at a predetermined height, heights, or range of heights, depending on the definition of the EML quota to be measured (see later). The EML levels may be mapped out on a per space basis, e.g. per room. I.e. there is at least one EML value stored for each room or space 2*a* (and in embodiments multiple values for e.g. different respective times of day and/or settings). This EML value per space or room 2*a* may be an average EML level taken at a particular height above the floor over some or all of the area of the space 2*a* in question (e.g. the room), in a particular direction or averaged over a range of directions (e.g. omnidirectional or semi cylindrical). Alternatively, the database 12 may store an EML value for each of one or more characteristic locations in each space (e.g. room) 2*a*. For instance, the database 12 may store an EML value for each work station, e.g. the EML in the typical direction the occupant 8 faces at that work station, or the EML averaged over a range of directions from that workstation. As another alternative, the information may be stored on a per luminaire 4 basis, along with coordinates of the luminaires. Knowing the EML emitted by the luminaire(s) 4 in a given space 2*a*, e.g. a given room, and the position of the luminaire(s) 4 and occupant 8, the controller 10 can thus compute the EML exposure of the occupant 8 at a given position at the predetermined height in question. As yet another example, the EML values for each space 2*a* (e.g. each room) may be mapped out in the database 12 on a relatively fine-grained point-by-point basis (i.e. for individual sets of coordinates within each room or space 2*a*), so as to create an EML "fingerprint" for each room. Further, the EML values in the database may or may not have a directionality. That is, in some cases, for each space 2*a*, station or point, the database 12 may store a single EML value which could be the EML in a particular characteristic direction or the EML averaged over a range of directions, e.g. an omnidirectional average (averaged around 360 degrees in the horizontal plane); or alternatively, for each space 2*a*, station or point, the database 12 may store multiple EML values for each of multiple different directions that the occupant may face when in that space 2*a* or at the point or station in question. Further different EML levels may be stored for different possible dim levels and/or colour settings, so the controller 10 can also take into account the current setting(s) of the luminaire(s) 4 in each space 2*a*.

In yet further variants, the information in the database 12 may be another measure of spectral light level, such as the lux level Ev along with the colour temperature or other spectral information, or even full power spectral density (PSD) data. From this, the controller 10 can then calculate how high the verticals or cylindrical illuminance are in a space, and this figure can be multiplied with the ratio (MEF) for the colour temperature or specific spectrum, which will result in the EML value for that space or specific position in space based on the artificial lighting. Everything said above about the different levels of granularity or directionality of the EML values can equally apply to any other data indirectly indicative of EML, such as lux & colour temperature (CCT), or PSD measurements.

The controller 10 is configured, based on the location of the occupant 8 as tracked by the tracking system 16, and based on the information in the database 12, to monitor the total EML exposure of the occupant 8 over a predetermined time window or windows, preferably over the course of a day or certain period or periods within a day. The controller 10 thus monitors whether the occupant 8 is exposed to at least a minimum EML quota for at least a minimum time period. The total EML exposure may be measured by integrating the actual EML exposure level over time (or performing a discrete integral over discrete time intervals). Preferably the total measure or dose resets each day (per 24 hours), e.g. every morning the occupant's EML count starts from zero again. The period is preferably 24 hours since EML is linked to the occupant's circadian rhythm. However, for people working in shifts or off-world such as on a space station, they may live an artificial life during a certain period and hence their circadian rhythm may become different and not synchronised with natural day/night cycles. And/or, it is not excluded that it may be desirable to measure an occupant's EML exposure over the course of a longer period such as a week. E.g. perhaps it may be acceptable (albeit not preferred) if the occupant receives a lower EML exposure on day per week as long as they receive a good exposure over the rest of the week.

In embodiments where the database 12 stores only a single average or representative value of EML per room or space 2*a*, the tracking and monitoring may consist of monitoring how long the occupant 8 spends in each room or space 2*a* and integrating the respective EML values over time. If on the other hand the EML information in the database 12 is more spatially granular, the tracking may comprise tracking the location of the occupant 8 within each room or space 2*a*, e.g. using an indoor location system, and integrating the EML as he/she moves about his/her path. Similarly, if the EML information in the database 12 has a directionality, the tracking may comprise tracking the direction the occupant is facing within each room or space 2*a*, and integrating the EML as he/she faces in different directions. For instance this may be done based on cameras and spatial recognition, or by tracking the direction of travel of the occupant 8 (on the basis that people usually face forwards in the direction of travel). In another example, the tracking system 16 may detect when the occupant 8 is stationed (e.g. seated) at a particular station (e.g. desk or other such work station) having a predetermined viewing direction associated with it. For instance when the occupant 8 is seated at his/her desk it may be assumed that the occupant is facing forward most of the time whilst at the desk, or if the occupant 8 is stationed at a work station having a screen then it may be assumed the user is mostly facing in the direction of the screen for most of that time.

In embodiment the controller 10 may be adapted to determine that the occupant 8 has not been exposed to a certain total EML quota by a certain time, e.g. a certain time in the day, or that it is unlikely that he/she will be, given the current time and the EML levels in the various spaces 2a, 2b, and then the controller 10 may be adapted to automatically take one or more measures to boost the occupant's EML levels. This may comprise increasing the intensity of one or more of the luminaires 4, or increasing the colour temperature (i.e. to a bluer colour), or both. Another possibility in some embodiments is to automatically open more fully one or more of the window treatments 5 (i.e. curtains or blinds), if controllable by the controller 10. As another alternative or additional possibility, the controller 10 may trigger one or more additional EML sources to boost the occupant's exposure, e.g. a dedicated EML device at the occupant's work station. Further, in embodiments the controller 10 may be adapted to determine that the user has already reached a certain total EML quota by a certain time, e.g. a certain time in the day, or is likely to, given the current time and EML levels in the various spaces 2a, 2b, and then the controller 10 may be adapted to automatically take action to turn off or reduce the intensity of one or more of the luminaires 4, or to reduce their colour temperature. Although there is not believed to be any maximum EML quota an occupant 8 might be exposed to, such measures may be beneficial for other reasons, such as to save power, or to create a more cosy "wind-down" atmosphere toward the end of the day. E.g. light with a relatively high colour temperature is not very cosy and people will tend to prefer warmer lighting. In addition there is also no need for the high vertical illumination at face height outside the "activation" or "stimulation" hours. Also it is not excluded that in the future it may be desired to avoid providing too much EML to avoid possible negative effects on the occupant 8, e.g. not sleeping well due to receiving too much blue light too late in the day, or at other time intervals.

In some embodiments, the controller 10 may be configured to attempt to predict the occupant's upcoming movements over the rest of the day, or more generally the rest of the time period or periods for which EML is being monitored. It can then use this predicted behaviour to assist in the estimate of whether the occupant 8 is likely to reach his/her EML quota for the day or period currently under observation. This prediction may be based on using the tracking system 16 to track the occupant's movements over one or more previous days or periods. For instance the controller 10 may determine based on past behaviour that the occupant 8 usually goes to a certain canteen or breakroom at lunchtime, and/or that he/she usually works at a given workstation or in a given room 2a for a certain part of the day (e.g. morning or afternoon), or perhaps that he/she often goes for a walk at lunchtime. In some embodiments, the controller 10 may be configured with a machine learning algorithm arranged to learn the occupant's behaviour over time. E.g. after a few weeks it could be possible to predict the behaviour of individuals, such that the system will recognize the person and know where he/she typically spends their time, so the system can start to know a person's agenda and make predictions. Alternatively or additionally, the controller 10 may be configured to predict the occupant's movements by analysing a personal agenda of the occupant 8 (e.g. calendar function integrated in an email client). I.e. the controller 10 can look into the agenda and predict where most time will be spend and how the received EML will be over time that day.

In further embodiments, instead of or in addition to adapting the light provided to the occupant, the controller 10 may be configured to output a message to be indicated to the occupant 8 on a suitable user interface. The message may indicate when the EML quota is not met or is predicted unlikely to be met (e.g. for the day), and/or to indicate when the EML quota is met or is likely to be met (e.g. for the day), or to indicate the current running EML quota so for (e.g. for the day). Alternatively or additionally, the message could be output to another user such as a supervisor of the occupant 8 (with consent from the occupant 8). The message may include useful advice to take a lunchtime walk outdoors. As another example, the message may give advice to help the occupant 8 to overcome a jet lag feeling or to prepare him/her for traveling to another time zone in the world, i.e. to recover from or prepare for a different circadian rhythm. The message may be output via any suitable user interface. For instance the controller 10 may transmit the message to a portable user device of the occupant to be displayed on a screen of the portable device, e.g. a smartphone, tablet, laptop or wearable device. As another example the message could be sent to be displayed on the screen of a static terminal such as a desktop computer at the workstation of the occupant 8, or his/her supervisor or lifestyle coach, or the message could be an audible alarm played in one or more of the rooms 2a, or a supervisor's room.

In some embodiments, the system further comprise at least one light sensor 6 installed in each room or space 2a. The sensors 6 are coupled to the controller 10 and thereby arranged to provide their sensor readings to the controller. The sensed sensor readings measure both the light power and an indication of spectrum of the light as received at the sensor's light sensing element. The indication of the spectrum could be a sensed colour temperature, or a full power spectral density measurement (power per unit frequency). Given the area of the sensor's sensor element it is also possible to determine the light power per unit area. Given all this information from the sensor 6, the controller 10 can thus automatically determine the EML at the point of the sensor 6. Alternatively the sensors 6 may only sense the intensity level and not the spectral information, but the controller 10 is configured with predetermined information as to the kind of luminaires 4 installed and their spectrum.

Each sensor 6 may be arranged at the height for which the EML quota is specified, e.g. 1.2 m above the floor. Each sensor may be arranged at the horizontal position at which the EML is to be measured for assessing the EML quota. Alternatively the sensor 6 could be arranged at a different height and/or horizontal position, and instead the controller 10 computes the EML at the specified height and desired position based on additional information about the position of the sensor 6 and the lighting devices 4, 5 or their relative position to the specific height and desired position.

The light sensor 6 together with the logic in the controller 10 as described above forms an EML sensor, arranged to automatically sense the EML level at a given height/position during the operational phase of the system. The controller 10 can then use the information derived from the sensor readings to determine where in the environment 2 the minimum EML level is met, and thereby monitor whether the occupant's EML quota is met. The sensors and logic may be used to supplement the information in the database 12, or as an alternative to it. Everything said above about the options for the EML values in the database 12 equally apply to the option of alternately or additionally using sensors 6. For instance, the sensor(s) 6 in each space may be used to determine a single representative or average EML value per room or space 2a, 2b; or with more than one sensor in each room or space 2a, 2b, a more spatially granular and/or directional map of EML values may be computed by the controller 10. Further, the sensors 6 may for example communicate wirelessly with the controller 10 and nowadays may be so cheap that all workstations can be monitored by at least one sensor, preferably directed in substantially the same direction as the occupant's face when stationed (e.g. sitting) in the intended position at the respective work station. The use of sensors also has the advantage that daylight can be taken into account, e.g. as entering through windows in indoor spaces 2a.

With regard to any outdoor spaces 2b, the EML will differ a lot depending on the season, time and weather conditions. Similar considerations apply to the contribution from any windows (which may also be modulated by window treatments 5). Using the sensor based approach, it will be possible to measure the real EML in real time with sensors 6. Alternatively or additionally, in further embodiments the controller 10 is connected to a communication network 14, e.g. a wide area network such as the Internet, enabling it to access real-time information on external light levels. For instance the controller 10 may access an online weather report. The weather report may not give explicit EML values per se, but it may provide information from which approximate EML values can be derived by the controller 10. For instance the weather report may report luminous intensity levels, or simply an indication of whether it is sunny or overcast or the like. From this, combined with a priori data on the typical spatial and spectral distribution of natural ambient light, the controller 10 can estimate an approximate EML level at the desired height above the ground. In embodiments the controller 10 may also take into account the layout and/or orientation of the space 2a, 2b in question, e.g. any high walls or trees in an outdoor space, and/or the size, shape and/or position of a window and status of its window treatment 5.

Another option is to use a calendar and provide average or typical minimum values for EML per day/week/month/season. So when going from one building to another via an outdoor space one can take the EML level of the day/week/month/season and multiply this with the time one is outdoors. EML can differ a lot depending on the weather, but minimum levels of EML can be linked to an agenda as a rough approximation. A variant of this would be to use one outdoor sensor 6 for the whole environment (e.g. campus).

Whatever means of measuring EML is used, the quota used by the controller 10 is defined for a specific height, heights or range of heights above the floor. For indoor spaces, "floor" may refer herein to the finished floor as specified by the WELL standard. For outdoor spaces the "floor" may refer herein to the ground. The height used may be 1.2 m above the floor in accordance with the WELL standard to approximate a typical eye height of a seated occupant 8. Alternatively or additionally other heights or ranges of heights could be used. For instance a height of 1.5 m could be specified to approximate standing height, as an increasing trend nowadays is for standing work stations, or indeed as some jobs are not desk based. In further embodiments, a range of heights from 1.2 to 1.5 m, or 1.2 m to 1.6 m, or 1.2 m to 1.7 m, may be used to cover the possibilities that the occupant may be standing or sitting, or may have and workstation with adjustable work surface height from seated to standing position. E.g. the EML used may be averaged of the range of heights, or the controller 10 may test whether the EML quota is met across the full range of heights.

As to the value, the current WELL standard specifies different EML values for different scenarios and these include 125 EML, 150 EML and 200 EML. A value of 250 EML was also proposed in a prior version of the WELL standard and is not excluded here. Any such value or others could be used for the present purposes.

As to the time constraint, this could be simply that the occupant 8 receives the total EML quota over a predetermined window of time such as a day, or the daylight hours of a day, or a working day (e.g. 9 am to 5 pm). Alternatively the criteria may be more complex.

For instance, for work areas the WELL standard defines that 200 EML is present (measured on the vertical plane facing forward, 1.2 m above finished floor) for at least the hours between 9:00 am and 1:00 pm. Another example of a more complex condition is that a minimal EML illuminance should be present for at least 4 daytime hours for every day of the year, preferably in the morning, with at least 2 of these hours between 8:00 am and 11 am.

Although particular combinations are set out in the WELL standard, the scope of the present disclosure is not bound by those, and other combinations of the above criteria and/or others can be applied. In general any EML level may be combined with any height and any time condition to define an EML quota.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining exposure of an occupant to equivalent melanopic lux, EML, in an environment comprising one or more illumination devices, the method comprising:

accessing light level information from one or more information sources, and based thereon determining where in said environment at least a predetermined EML level is present;

using a tracking system to track the occupant within said environment; and based on said accessing and said tracking, monitoring whether the occupant has been exposed to at least a minimum EML quota, the minimum EML quota comprising the occupant being exposed to at least said predetermined EML level for at least a predetermined time constraint; wherein the illumination devices comprise one or more luminaires illuminating the environment with artificial illumination,
wherein the one or more information sources comprise a database and said light level information comprises data from the database mapping out light level values indicative of EML in said environment, wherein the light level values are pre-calculated or pre-measured and obtained during a pre-performed calibration of the one or more luminaires during an installation or commissioning phase, said determination being based at least in part on the light level values.

2. The method of claim 1, wherein the environment comprises one or more outdoor spaces, and/or the environment comprises one or more indoor spaces and the illumination devices comprise one or more window treatments; and wherein the light level information comprises dynamic information on natural daylight, said determination being based at least in part on said information on the natural daylight.

3. The method of claim 2, wherein the one or more information sources comprise a communication network providing a report on current daylight conditions, said determination being based at least in part on said report.

4. The method of claim 1, wherein the one or more information sources comprise a network of light sensors, each sensor arranged to measure light level information at a different respective horizontal location within the environment, said determination being based on said measured light level information.

5. The method of claim 1, comprising using a timer in conjunction with said accessing and tracking to predict whether the occupant will be exposed to said predetermined EML quota, and if not, perform one or both of:
automatically controlling the illumination to increase the EML level in at least one region of the environment that the occupant is occupying or is predicted to occupy later; and
automatically reducing an intensity and/or colour temperature of at least some of the illumination, or switching off at least some of the illumination, so as not to meet said predetermined EML level in at least one region of the environment where the occupant is determined not to be currently present based on said tracking, or after the occupant has already been exposed to the minimum EML quota or it is predicted that the occupant will be exposed to more than said minimum EML quota.

6. The method of claim 1, comprising, based on said accessing and tracking, automatically informing the occupant or another user via a user interface one or more of:
whether the occupant has been already exposed to the minimum EML quota,
whether it is predicted the occupant will be exposed to the minimum EML quota, and/or
a running measure of current EML exposure of the occupant.

7. The method of claim 1, wherein the predetermined EML level is the EML at at least one predetermined height above the floor.

8. The method of claim 7, wherein said predetermined height is one of:
between 1.2 and 1.7m,
1.2m, or
1.5m.

9. The method of claim 1, wherein said predetermined EML level is equal to or greater than 125 EML.

10. The method of claim 1, wherein said predetermined time constraint comprises at least a requirement that the occupant is exposed to said predetermined EML level for a minimum period of time within a predetermined time window of a day, a working day, the hours of daylight in a day, or a morning between 9 am and 1 pm;
wherein the time constraint resets each day.

11. The method of claim 1, wherein one of:
said predetermined time constraint is that the occupant is exposed to at least said predetermined EML level for at least three hours between 9 am and 1 pm; or
said predetermined time constraint is that the occupant is exposed to at least said minimum EML level for at least 4 daytime hours during the day, with at least two of the daytime hours during the day between 8 am and 11 am.

12. Control apparatus for determining exposure of an occupant to equivalent melanopic lux, EML, in an environment comprising one or more illumination devices wherein the illumination devices comprise one or more luminaires illuminating the environment with artificial illumination, the control apparatus comprising:
means for operatively coupling the control apparatus to one or more information sources for accessing light level information for the environment, wherein the one or more information sources comprise a database and said light-level information comprises data from the database mapping out light level values indicative of EML in said environment, wherein the light level values are pre-calculated or pre-measured and obtained during a pre-performed calibration of the one or more luminaires during an installation or commissioning phase, said determination being based at least in part on the light level values;
means for operatively coupling the control apparatus to a tracking system for tracking a position of the occupant within said environment;
the control apparatus being configured to, based on said accessed light level information and said tracked position, monitoring whether the occupant has been exposed to at least a minimum EML quota, wherein said minimum EML quota is defined as the occupant being exposed to at least said predetermined EML level for at least a predetermined time constraint.

13. A system for determining exposure of an occupant to equivalent melanopic lux, EML, in an environment, the system comprising:
one or more illumination devices for illuminating the environment;
one or more information sources for accessing light level information for said environment;
a tracking system for tracking a position of the occupant within said environment;
a control apparatus according to claim 12 and further configured to use a timer in conjunction with said accessed light level information and said tracked position to predict whether the occupant will be exposed to said predetermined EML quota, and if not, perform one or both of:
automatically control the illumination to increase the EML level in at least one region of the environment that the occupant is occupying or is predicted to occupy later; and
automatically reduce an intensity and/or colour temperature of at least some of the illumination, or switch off at least some of the illumination, so as not to meet said predetermined EML level in at least one region of the environment where the occupant is determined not to be currently present based on said tracking, or after the occupant has already been exposed to the minimum EML quota or it is predicted that the occupant will be exposed to more than said minimum EML quota.

14. The sytem of claim 13, wherein the one or more information sources comprise a database comprising light level information mapping out light level values indicative of EML in said environment wherein the light level values are pre-calculated or pre-measured obtained during a pre-performed calibration of the one or more luminaires during an installation or commissioning phase, and/or a network of light sensors each sensor arranged to measure light level information at different respective horizontal locations within the environment.

* * * * *